United States Patent
Virtanen et al.

(10) Patent No.: US 8,493,220 B2
(45) Date of Patent: Jul. 23, 2013

(54) ARRANGEMENT AND METHOD TO WAKE UP A SLEEPING SUBJECT AT AN ADVANTAGEOUS TIME INSTANT ASSOCIATED WITH NATURAL AROUSAL

(75) Inventors: Väinö Virtanen, Vantaa (FI); Aino Salmi, Vantaa (FI); Seppo Salmi, Helsinki (FI)

(73) Assignee: Smart Valley Software OY, Vantaa (FI)

( * ) Notice: Subject to any disclaimer, the term of this patent is extended or adjusted under 35 U.S.C. 154(b) by 796 days.

(21) Appl. No.: 12/527,257

(22) PCT Filed: Feb. 12, 2008

(86) PCT No.: PCT/EP2008/051693
§ 371 (c)(1),
(2), (4) Date: Sep. 2, 2009

(87) PCT Pub. No.: WO2008/098943
PCT Pub. Date: Aug. 21, 2008

(65) Prior Publication Data
US 2010/0102971 A1      Apr. 29, 2010

(30) Foreign Application Priority Data
Feb. 15, 2007   (FI) ...................................... 20070135

(51) Int. Cl.
*G08B 23/00* (2006.01)

(52) U.S. Cl.
USPC ........................................ 340/575; 340/309.4

(58) Field of Classification Search
USPC ............... 340/575, 309.4; 600/26, 27; 386/46
See application file for complete search history.

(56) References Cited

U.S. PATENT DOCUMENTS

| | | | |
|---|---|---|---|
| 4,245,651 A | 1/1981 | Frost | |
| 4,306,567 A | 12/1981 | Krasner | |
| 4,832,050 A | 5/1989 | DiLullo | |
| 2003/0096580 A1 | 5/2003 | Kaplan | |
| 2003/0236474 A1 | 12/2003 | Singh | |
| 2004/0257233 A1 * | 12/2004 | Proebsting | 340/573.1 |
| 2005/0012622 A1 | 1/2005 | Sutton | |
| 2005/0143617 A1 * | 6/2005 | Auphan | 600/26 |
| 2005/0154330 A1 | 7/2005 | Loree, IV | |
| 2005/0190065 A1 | 9/2005 | Ronnholm | |
| 2007/0083079 A1 * | 4/2007 | Lee et al. | 600/27 |

FOREIGN PATENT DOCUMENTS
EP     1 247 488     10/2002

OTHER PUBLICATIONS

International Search Report dated Aug. 18, 2008, from corresponding PCT application.

* cited by examiner

*Primary Examiner* — Shirley Lu
(74) *Attorney, Agent, or Firm* — Young & Thompson

(57) ABSTRACT

Intelligent alarm clock arrangement adapted into an electric device and utilizing the microphone, loudspeaker or other alarming device, memory unit, processor and timer feature thereof. The apparatus is located near a sleeping subject so as to sample and analyze the statistical properties of sound signals produced by the movements of the sleeping subject and to classify the sleep states according to the analyzed signals into a peaceful calm deep sleep, a light sleep with arousals and awake periods associated with the movements. An alarm wakes up the subject during a pre-programmed time window, if there are arousals, awake state and movements present at that time to induce the awakening at a biologically advantageous instant. Instead of the local alarm function, the device may perform a remote alarm using a call or sending a message to a pre-programmed phone number when the awakening of the sleeping subject is detected.

20 Claims, 4 Drawing Sheets

Figure 1:
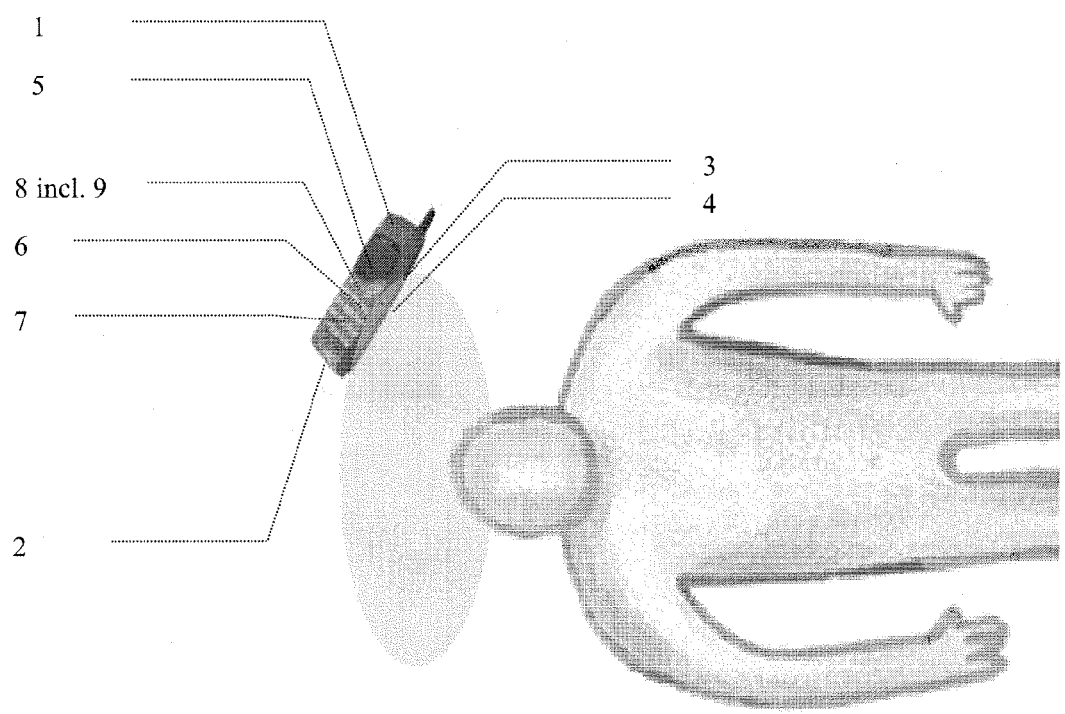

ARRANGEMENT AND METHOD TO WAKE UP A SLEEPING SUBJECT AT AN ADVANTAGEOUS TIME INSTANT ASSOCIATED WITH NATURAL AROUSAL

FIELD OF THE INVENTION

In general, the invention relates to the use of the electronic devices in sleep research. Specifically, the invention relates to the use of the aforementioned devices in the recording and analysis of the sounds produced by the sleeping subject and in the detection of the arousals of the subject on the basis of the analysis.

BACKGROUND OF THE INVENTION

The sleep-wake rhythm of humans generally consists of the wakefulness during day-time and the sleep during night-time. The time in sleep is not a homogenous period of time but consists of different phases of sleep called "sleep stages" including Stage 1 to Stage 4 (S1-S4) and REM (rapid eye movements) stages, which can be detected and characterized using the electrophysiological measurements called polysomnography. A typical feature of different sleep stages is that the stimuli to wake up the sleeping subject are different. During the wakefulness the stimuli are followed actively by the subject. In drowsiness and very light sleep (Stage 1) the stimulus to awake is small and in the deep sleep ("slow wave sleep", i.e. Stage 2 and especially Stage 3-4 and REM sleep) the stimulus required is strong and the wakening up the person and the awakening experienced by the sleeping subject are difficult and the awakening is experienced troublesome and unpleasant. The sleep stages succeed each other after the onset of the sleep. First the sleep becomes deeper and thereafter the deepness of the sleep varies in repeated periods (sleep cycles) of about 90 minutes. Between the sleep cycles the sleeping subject often changes his/her body position and then the sleep is especially light during the body movements and the sleeping subject is actually awake during the short periods of movements to refall asleep immediately. The sleep cycle is clear and regular during the first, evening hours of the sleep but it becomes more irregular during the dawn (last) hours of the sleep and the body movements, changes in body position, and changes of the sleep stages into deeper and lighter sleep are more frequent during the last hours of the night sleep. It is typical in many sleep disorders, including insomnia, that the cycling pattern of the sleep constructed by the different sleep stages becomes irregular and poor.

During the deep sleep ("slow wave sleep" in electrophysiological measurements like PSG) the muscle tone of the sleeping subject is very low, the breathing (respiration) is peaceful and there are no special movements of the body or the limbs present. During the REM sleep the muscle tone is very low but very short movements like twitches of muscles may still take place. The typical feature of REM sleep is the rapid eye movements setting the name to the whole sleep stage. REM sleep is present predominantly during the last hours of sleep. During REM sleep and these short twitches of the muscles the wakening and awakening is not easy. The duration of the changes in the body and limb positions is several seconds. These movements are possible only using the big body muscles so that the sleeping subject in the electrophysiological measurement is actually detected to be awake for a short period of time although he/she cannot remember it afterwards.

If the duration of the night sleep is sufficiently long, the awakening may happen spontaneously and without any troubles in the morning when there is no more pressure to sleep and the sleeping subject feels vigilant and alert. If the sleep-wake cycle is regular and the amount of the sleep is sufficient, the human body with the internal rhythms of the brain and the other organs may even learn to awake spontaneously regularly without any alarm clock. The schedules may not always be regular, however. Because the social schedules also are important and the sense of elapsed time is not present during the sleep, an alarm clock is often required to wake up the sleeping subject at a specified, fixed time of day. It the alarm clock is alarming during the deep slow wave sleep or during REM sleep the awakening may be especially troublesome, slow and even an unpleasant experience. If the awakening occurs at a moment when the sleeping subject is in light sleep (in drowsiness) or e.g. changing the sleeping position (arousal) and therefore actually awake, the awakening takes place easily without troubles and even due to a minimal stimulus, which also may be a natural stimulus like voice, light, or other similar stimulus from the surrounding. This kind of awakening during the drowsiness (light sleep) or during spontaneous arousal or the wake state is thus obviously advantageous to the human organism and well-being. The wake-up due to the alarm clock at an accurately fixed time point may obviously happen either advantageously during light sleep stage or unfavourably during the deep sleep.

When the quality of sleep of a sleeping person, especially of a baby, is monitored, the parents of the baby or the other persons wish to monitor and follow up the well being, calmness and awakenings of the sleeping child. The voices due to crying may be monitored from distances using a wireless radio frequency transmitter ("cry detector") located near to the baby which allow the parents in another room to notice that their baby is crying and not sleeping. In that case they may come to look for the status of the baby and, if required, peacefully pacify the baby to induce sleep again. These alarming devices are thus used to detect that the sleeping subject has awakened. The detection of the awakening of the baby is based on the detection of signals which are higher than the triggering level which has been set as the criterion for the alarm.

One prior art solution to wake up a person is called "Sleep Tracker" (www.sleeptracker.com) based on the publication "Easy Wake Wrist Watch" US 2005/0154330. This device is a "wrist watch" combined with a movement sensor (sensor for acceleration, "actigraph"). The device is monitoring the movements of the body using the signals from the acceleration sensors throughout the night and it aims to notice different kinds of sleep stages (stage with no movements as the deep sleep and movements during transitions between the sleep stages). The user of the device determines a time window which is the time period during which he wants to wake up. If the device detects, using the signal from the movement sensor, an advantageous type of epoch of a sleep cycle, the alarm clock of the wrist watch performs the wake up. Same type of methods and devices to detect arousal state has been based on the analysis of brain electric activity (electroencephalography) and eye movement electric activity (electrooculography).

The aforementioned devices have to be purchased separately (the sensor and alarming device fixed to the wrist, separate sensor and alarming devices, amplifiers, measuring devices of EEG or EOG signals). The present methods also often require the sensor devices to be fixed permanently to the sleeper causing discomfort and making sleeping troublesome. In addition, if utilized outside permanent home, the devices have to be carried along and be prepared for use. Accordingly, prior art solutions are often prone to various environmental conditions that may deteriorate the performance of used measurement and analysis methods in real-life scenarios wherein the prevailing conditions often differ from time to time.

SUMMARY OF THE INVENTION

The objective of the present invention is to alleviate at least some of the aforesaid defects of prior art solutions. This objective is met by the method and the arrangement in accordance with the present invention, see the characterizing portions of claims 1 and 8, respectively, the arrangement preferably being or at least including a personal mobile device, e.g. a mobile cell phone or a small personal computer (PDA, personal digital assistant), adapted to detect movements of a sleeping person based on voice and/or other sound signals generated by the movements, and to analyze, preferably with continuous statistical analysis, the sound signal(s) in order to detect a likely arousal or awakening of the person. A further goal of the embodiments of the invention is to wake up the sleeping person within a desired, predetermined time period (hereinafter referred to as an awakening-time-window) when he/she is making some movements and thus most probably is in light sleep or in the wake state when indicating that the awakening and the wake-up action are easy and natural processes instead of the person being in deep sleep when the awakening is troublesome. As another application the device may be configured to detect a probable awakening of the sleeping subject and send an alarm message to a person who is interested in the state of the sleeping person. One or multitude of the functions to be performed after the detection, e.g. wake up alarm or sending the alarm messages, may be implemented using typical features of the aforementioned electronic devices available to wake up, alert and send messages. The desired action may thus be advantageously utilized by the user without purchasing any extra equipment but e.g. by loading specific computer software into the personal mobile communication and data processing device(s) to perform the analysis, wake-up and alarm functions. The computer software (product) may be, optionally separately, delivered for a suitable electric device e.g. using storage or transmitting medium like magnetic disc, memory card, memory stick, optical disk, or utilizing (wireless) transmission over communication networks such as the Internet.

In one embodiment of the invention an arrangement comprises a microphone to monitor the sound signals produced by the movements of the sleeping person, e.g. by rustle of the bed clothing or the pillow. In addition, the arrangement incorporates a clock and timer to accurately determine the right point of time for the recording and alarming functions required, preferably further incorporating a programmable processor unit to execute a computer software to analyze the amplitude, power and/or spectral characteristics and/or the duration of the sound signals and a means for performing the wakening up, e.g. an alarming unit. The electronic arrangement includes a keyboard, control panel, or related tools for the user to activate and close the functioning system. It may also comprise a display unit to make it possible for the user to monitor the required settings (e.g. the time of day) and to see the graphic output of the detected movements during the night time. If required, the information transmitting units of the device (e.g. a radio frequency transmitter or a transmitter-receiver) are used to send an alarming message to an external site or person who is interested in the possible arousal and awakening of the sleeping subject. Typically and advantageously all these components are present and form an integral part of the modern mobile cell phones ("smart phones"), personal lab-top and smaller (palm sized) computers, or PDAs (personal digital assistant"). The specific wakening and alarm functions may be achieved by constructing and loading the specific computer software with aforementioned features and functions into the mobile cell phone, personal small computer (PDA) or other suitable (personal) device of the user.

The goal of the invention may be promoted and the rustle of the bed clothing and other bed materials, when the sleeping person is moving during the sleep and arousals, may be amplified and modified using a proper material, which modifies the spectral frequency and/or amplitude characteristics of the sound signals; this material could be configured such that it at least partially surrounds the measuring device, the microphone of the device, or said material could form a part of bed clothing or a sleeping suit. This material may be e.g. plastic sheet, other material of synthetic or natural origin to be part of the bed clothing or sleeping suit. The material for this purpose may also be a bag or pocket of similar material to accommodate and fix the microphone unit of the measuring device to the immediate vicinity of the sleeping subject, e.g. to the bed clothing. This vicinity may also refer to the pocket of the sleeping suit or a separate bag hanging around the neck of the sleeper, for example. The microphone unit may also be positioned next/near to the sleeping subject or in the surrounding space located so as to utilize the sensitivity of the recording to detect any sound signals produced by the movements. This sound signal is generated with higher power and it is transmitted louder and with more advantageous frequency characteristics into the microphone unit when the specific movement is applied against the sensitizing material. This is a tool to increase the sensitivity and specificity of the measurement, to decrease the probability of other voices and sound signals produced by external noise generators (like air-condition or home electronics etc), by movements or other actions of a possible another sleeping person sharing the bed, or by the sleeping person (breathing voices and snoring) which all could disturb and confuse the detection of the target body and limb movements.

The sensitivity of the measurement may also be increased using the statistical analysis of the signals during the measurement and detections. The audio signal from the microphone is converted into digital format for the processing analysis software. The frequency content with mainly noisy signals and thus artefacts is rejected. This may be performed using e.g. the digital filtering process of the analysis software. The sound signals produced by the movements are detected and identified using e.g. typical power (amplitude), frequency contents, duration and/or distribution of the signals as the criteria.

The analysis of the measurement is directed to the signals due to the movements during the otherwise calm night sleep generally omitting such movements. The analysis software of the processor of the electronic device is configured to process the sampled data (signal) using statistical analysis methods, and the software tries to continuously identify characteristics of the typical background noise and determine e.g. the average (loudness) level of the background sound signals. This noise level may be caused by the sleeping subject (snoring, breathing voices etc) or be produced by the noises of the environment of the sleeping subject (air-conditioning, electronic devices, and other disturbing noises from the environment). The typical background noise level may be determined statistically e.g. by calculating a moving average of the signal amplitude or by median (filtering) of the signal. Values that exceed the statistically determined average background noise level in the sound signal may be interpreted as significant and further analysis can be then directed to those signals. Using this type of continuous statistical analysis it is possible to make an adaptive analysis of the signals and to apply the analysis to different kind of environments and to any changes in the environment, body position, and distance between the sleeping person and the microphone unit during the night time, which changes may affect on the sound signals recorded by the method and device.

The mobile cell phones and personal small computers (PDA) often include the aforementioned microphone unit, memory and processing capacity, a real-time-clock, a timer and different functions for wakening and alarm. They may also generally comprise sufficient battery capacity, timing and alarming functions for long-term monitoring and may further support various alarm modes using sound signals, light, and mechanical (vibratory) alarming functions. The quality and loudness of the alarming stimuli can be preferably modified by the user. These advantageously developed standard features of the electronic devices may be used as such without at least substantial modifications. These applicable electronic devices are designed to be stored and carried continuously by the users, e.g. in their pockets, and they are physically small in size and have a strong construction. The standard components often include keyboard (or ~keypad) and display units to be used for setting the timer or the alarm parameters, for example. The devices may include a keyboard lock or a keyboard cover protecting the keyboard and protecting the device from unintentional use that might possibly cause erroneous functions; such features are advantageous in the context of the present invention.

In another embodiment of the invention the mobile cell phone or another applicable apparatus includes, or the user of the phone loads into the phone, the aforementioned computer software which is configured for use as a smart wakening tool. The user initiates the execution of the software in the memory of the cell phone and sets the time of day which is the last desired moment he/she wants to be wakened-up, and the time of day, before which he/she does not want to be wakened. This preferred period of time is called an awakening time window. The user places the mobile cell phone under the pillow, inside the pillow or otherwise near to the bed clothing and goes to sleep. During the night-time before the awakening time window the computer software monitors the rustle and sound signals produced by the movements of the head and body of the sleeping subject directed against the pillow and bed clothing.

When the sleeping subject is in deep sleep there are no movements. When the sleeping subject is in REM sleep, some small and short twitch-like movements may take place, causing possibly some very short peaks of sound signals. When the sleeping subject is changing his/her sleeping position or makes movements when in awake or otherwise active state due to arousal, the microphone unit of the mobile cell phone is recording and storing sound signals with high power, high amplitude, and long duration. These several, e.g. three, different levels of the sound signals detected during the night time are used statistically to compute the statistical estimate on that the sleeping subject is in deep sleep, REM sleep or very light sleep, or in the awake state. When the awakening time window, which was preferably set by the user, is entered, the computer software is adapted to continuously monitor the movements of the sleeper using the sound signals detected by the microphone as the criterion. If the statistical analysis detects with a significant probability that the sleeper is in very light sleep (arousal) or awake, and thus in that occasion he/she is moving with significant power (high amplitude of the signals) and the duration of the high amplitude movement signal is significant, the mobile cell phone makes an alarming stimulus. This is performed using the normal alarming stimulus and functions of the cell phone (buzzer voice signal, vibration, flashing light, etc). If the active state of the sleeper, which statistically indicates a light sleep or an awake state, is not detected during the awakening time window, the mobile cell phone is configured to perform the regular wake-up when the end moment of the awakening time window is achieved. The user stops the wakening stimulus and the wakening computer software.

In another embodiment of the invention the user launches in his small personal digital assistant (PDA) device, or another suitable device, the smart wakening software of the present invention which he/she has purchased using the Internet connection, for example. The PDA computer is small in size, battery driven and provided with an external wired or wireless connection of a microphone unit, and with a loudspeaker. The user sets the aforementioned awakening time window to the software as input.

The user places the microphone unit connected to the PDA computer device into a bag or another object, or at least brings it into connection with the bag or object, manufactured of a noise producing (rattling) material, such as plastic material, and the bag is located under the bed clothing to have the rattling sheet partly beneath the sleeping subject and under bed clothing (like pillow) and the PDA computer is located at a greater distance like on the edge of the bed or on the table beside the bed. The sheet material of the microphone bag is configured to amplify the sound signals produced by the movements of the sleeper and to modify the frequency contents of the signals so as to increase the sensitivity of the microphone to detect the signals. The sheet material is located under the sleeper without disturbing the sleep. The advantageous material thus may be in contact with the sleeping object of the measurement but is still preferably separated from the possible other person sleeping in the same bed. Prior to entering the awakening window the computer software is configured to monitor the movements of the sleeping subject and, using the statistical analysis of the captured sound signals, to identify aforementioned the sound signal levels corresponding to the deep sleep, REM sleep and the powerful sound signals of long duration produced by the movements during arousal and wake state. The computer software may perform digital filtering of the sound signal to eliminate e.g. the low frequency noises, and it may calculate and determine the typical background noise level e.g. using median and/or mean values of the signals. After reaching the aforementioned awakening time window, the computer software again monitors the sound signal amplitudes and duration of significant sound signals advantageously using e.g. the (fixed) sampling rate of the sound signals. If the computer software detects in the continuous statistical analysis a sound signal of sufficiently high amplitude and long duration, it may be interpreted as significant movement of the sleeping subject. Accordingly, the computer software performs a wake-up function using a sound signal like 'buzzer' through the loud speaker unit of the computer. It there are no obvious arousals or awakening during the awakening time window detected by the computer, the software executes the wake-up procedure at the end of the awakening time window using e.g. the buzzer sound signal of a longer duration. The user stops the wake-up stimulus after his/her awakening. He may preferably see and visually analyze the movement detections during the last night on the display unit of the computer and estimate the quality of the sleep using this graphic output.

In a third embodiment of the invention the computer software with the aforementioned features to detect statistically instants and/or periods when a sleeping subject (e.g. a child or a baby, or an animal) is considered to be in calm deep sleep and when he/she is in awake state is installed into an electronic device like into a mobile cell phone. The statistical criteria and parameters include the duration and/or the amplitude level (or e.g. power) of the sound signals produced by movements and detected using the microphone of the device. The mobile cell phone is located to the immediate vicinity of the sleeping subject, such as a baby, by, for example, fixing it to the bed clothing or to the bed, and it is configured to monitor the sound signals produced by the sleeping subject and analyze the signals so as to classify the state of the sleeping subject into "calm, peaceful sleep state" (deep sleep=no movements and REM sleep=no movements with long duration) and into "awake state" (restless state with movements, voices and vocalisation). During the peaceful period of the sleep the computer software preferably performs statistical analysis of the features of the sound signal associated with the sleep states and stores the analysis results. During the awake state and awakening there are statistically significantly more sound signal periods associated with the movements of the subject. After a significantly long duration of the "awake state" detected by the analysis software, the software is configured to trigger an alarm by sending a phone message or phone call or a special text message (e.g. SMS, Short Message Service), or a graphic message (e.g. MMS, Multimedia Messaging Service), or a video message (e.g. MMS) or some other communication (message) of similar type to the phone or other communications device associated with a pre-programmed number or other address data of the person involved in monitoring the sleeping subject. By these means the information is sent to the monitoring party indicating that the person, whose sleep is actively followed up and monitored, is actually awake. This is also an option to inform the parents of the baby that the baby has awakened and is restlessly moving and/or crying.

In a fourth embodiment of the present invention, the device and method as described hereinbefore are utilized in another remote surveillance application as an antitheft alarm. Indeed, in this and many other embodiments the device may be configured to capture sound data via the microphone thereof and to analyze the captured sound data so as to determine whether significant events, according to predetermined fixed or adaptive criteria, are taking place in the environment. For example, the signals the amplitude, power, and/or duration of which exceed a selected fixed or adaptive threshold may be considered as indicative of interesting physical activity in the environment, and an alarm is triggered as a response. The alarm may be a local auditory alarm and/or visual alarm, or additionally/alternatively a remote alarm such as an alarm message sent to a remote receiver, the message preferably causing an auditory and/or visual alarm at the remote end. The response to the alarming situation may also encompass a picture or a video clip taken by the camera included in or connected to the utilized mobile phone or PDA apparatus.

As described herein relative to various embodiments the device of the present invention may be configured to dynamically change the parameters used for capturing and/or analysing sound signals from the environment thereof. For example, prior to entering the awakening window the device may be adapted to regularly (as controlled by a timer, for example), but not all the time, capture and/or analyze the sound data such that the underlying algorithm may adapt to the prevailing environmental conditions, e.g. various background noises not originated by the movements of the subject, and/or to general sleep behaviour of the subject based on the sounds caused by the subject himself. For example, a predetermined filter may be configured to model the (quasi)static background noise whereas the sounds deviating, according to selected criteria, from the average noise may be then utilized in modeling the sleep conditions of the subject. Upon entering the awakening window the monitoring may turn continuous such that advantageous time instants for natural arousal are not missed etc. Alternatively, the measurements may be done intermittently or continuously during the night, but the level of analysis may be altered dynamically, or on the basis of a number of time windows, e.g. a 'pre-window' and subsequent awakening window. In one further embodiment, the device is provided with a power supply and processing/memory means that actually enable performing continuous monitoring of environmental sounds throughout the overall measuring period, e.g. one night.

Adaptive factors that may be changed during the overall measuring period may include, but are not limited to, one or more elements selected from a group consisting of: sampling rate, number of bits per sample, recording period, interval length between recording periods, data storage method and/or parameter(s), amplitude/magnitude/power/duration threshold for defining an (in)significant event, applicable background noise modeling method, applicable sleep statistics analysis method, alarm type, and alarm length. Adaptation may be implemented and/or triggered in response to pre-programmed information (e.g. time windows), current battery status, current memory status, current processor load status, based on captured sound information and analysis thereof, and on receipt of external commands obtained via available communications means, for example.

In addition to or instead of acoustic monitoring, also visual monitoring via a camera may be utilized in the context of the present invention for triggering the alarm as mentioned hereinbefore. For example, a cell phone or a PDA may include both a microphone and a camera. Also external cameras connectable to the analysis arrangement may be exploited. The camera may be a black-and-white/monochromatic camera, a colour camera, or an infrared (e.g. night-vision) camera, for example. Image data captured by the camera (e.g. snapshots or movie/video frames) may be analysed and movements recognized therefrom. The recognition may be based on selected one or more visual pattern recognition techniques, for example. The movements may optionally be also categorized on the basis of such analysis. Image data may used to support decision-making procedure utilizing also the sampled acoustic signal, for example. The camera or the apparatus including the camera may be located close to the sleeping subject, e.g. on a nightstand or other object. The camera may also be used to take a picture or a video clip of the surrounding space and objects the apparatus is monitoring as one possible response to the alarm triggering. Thus even a picture or a video of the disturber or a thief, or other entity (e.g. baby), may be taken and stored and/or sent to the remote receiver.

DESCRIPTION OF THE ATTACHED DRAWINGS

Figure 2:
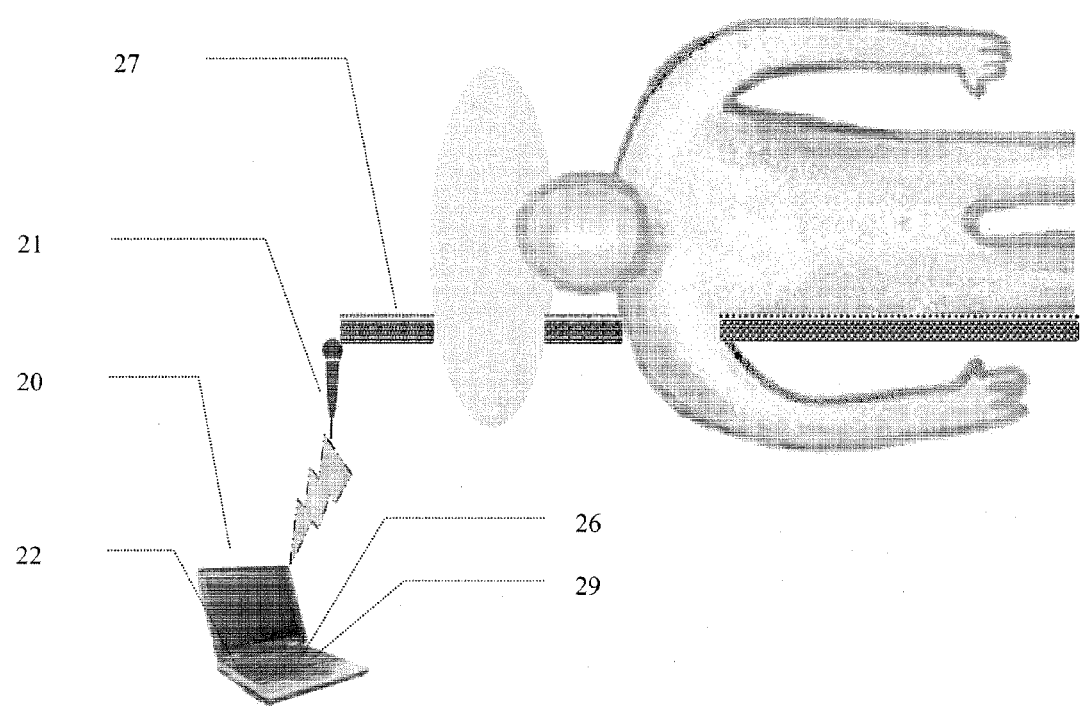
Figure 3:
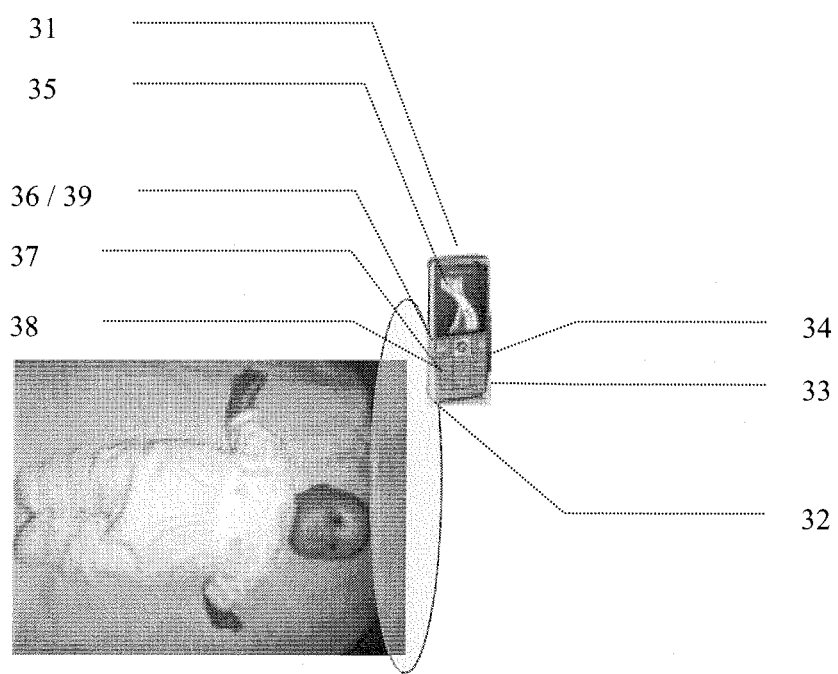
Figure 4:
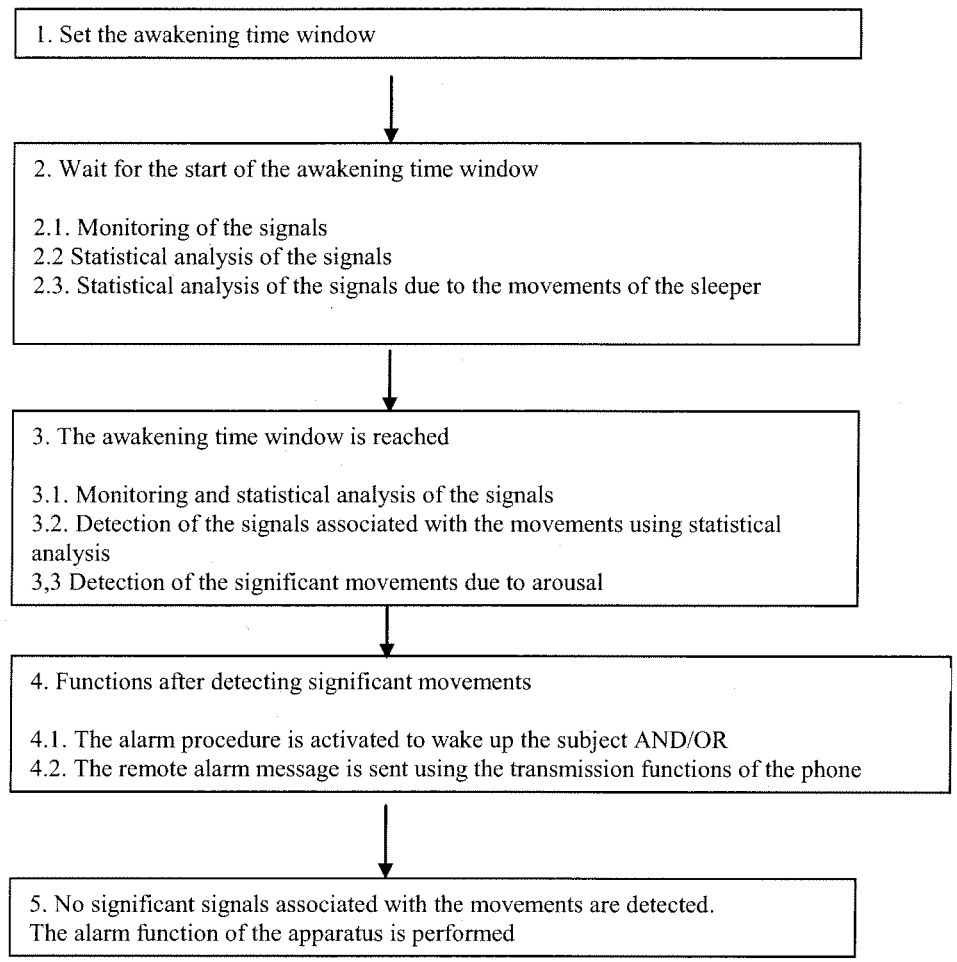

FIG. 1 visualizes an embodiment of the invention wherein a mobile cell phone is used as a smart alarm clock, FIG. 2 visualizes another embodiment where the device used for recording and analysis is supplied with a sheet material amplifying the sound source in interest, FIG. 3 visualizes an arrangement and device for the detection of the awakening of a baby via remote monitoring, and FIG. 4 discloses a flow diagram of the computer software of one embodiment for detecting a proper moment of spontaneous arousal to awake the subject during the sleep.

DETAILED DESCRIPTION OF THE EMBODIMENTS OF THE INVENTION

The FIG. 1 discloses the first advantageous embodiment of the invention. In the FIG. 1 the mobile cell phone 1 is used as the recording device and it is supplied with a microphone 2, a speaker 3, a vibratory alarming component 4 and a display unit 5. The mobile cell phone may be a so-called smart phone. The phone 1 may further include processor(s) 6, memory unit(s) 7 and timer(s) 8. The processor/memory may be supplied with the computer analysis software to perform the actions and processes described e.g. in the flow diagram of the FIG. 4 to be described hereinafter.

The user has set a time window for the desired moment of awakening in the morning to the mobile device. The mobile 1 has been located near to the sleeping subject e.g. under the pillow to facilitate detecting the sound signals produced by the movements of the head and upper body of the sleeper against the bed clothing, for example. The mobile cell phone 1 may sample the sound signals produced by the movements of the sleeping subject at regular intervals, using the microphone, the timer and pre-programmed sampling frequency, and store the data into the memory unit of the processor prior to reaching the awakening time window. Using statistical analysis of the sound signals the analysis software calculates the probabilities for the time epochs and classifies the epochs into epochs with high probability that the sleeping subject is in calm peaceful deep sleep or in REM sleep or into epochs with movements indicating an arousal (awake state) or in very light sleep according to the flow chart in the FIG. 4, for example. The computer software advantageously also stores at regular intervals the detected and processed signal values into the memory unit 6 using e.g. the timer 7 or some other timing feature. After reaching the beginning of the awakening window time period, when the user wants to trigger his/her personal wake-up alarm signals, the computer software in the processor 5 is configured to perform continuous statistical analysis of sound signals detected since then and classify the recorded and stored data as indicated in the flow-chart of the FIG. 4. If the probability of that the sleeping subject is awake (an arousal state) or in very light sleep is high according to predetermined criteria, for example, the alarming system (3, 4, 5) of the mobile cell phone may trigger an alarm signal. If no awaken state (arousal) or very light sleep is detected during the time period determined as the awakening time window, the alarm signal may still be produced at the end of the awakening time window using the alarm system of the electronic device.

In FIG. 2 another advantageous embodiment of the invention is visualized. In FIG. 2, a portable and preferably small-sized electronic device, e.g. a palm size personal computer (PDA) optionally equipped with rechargeable batteries 20 is supplied with a wired or wireless microphone 21 and a loudspeaker 22. The analysis computer software 29 is, according to one embodiment of the invention, downloaded using an Internet connection into the memory unit 26 of the computing unit of the device. The user triggers the execution of the computer software and sets the time moments for the start and end of the awakening period called the awakening window. Alternatively, the window may be determined via a start instant and window length, for example. Prior to the night time or another measurement period the user places the microphone of the device to reside close to a plate, a slab or the bed sheet 27 manufactured from a rustling or rattling material, e.g. membrane, situated under the sleeping subject with the microphone being in contact with or within short distance to the sheet, while the computer device being possibly located further away from the sleeping subject e.g. on the edge of the bed, or on the table at the bed. The membrane is amplifying the sound signals produced by the movements; it preferably modifies the frequency of the sound due to the movements to be easily detected and sampled by the microphone.

The membrane is thus used to advantageously increase the sensitivity by amplifying and transforming the sound signals, and to increase the specificity while the membrane reacts (due to the proper location of the membrane material) only relative to the movements of the subject in question, and thus e.g. the percentage of the sound signals produced by the movements of another person sleeping in the same bed compared to the total amount of the sampled sound signals is advantageously decreased. The membrane with such advantageous properties may be located e.g. to be part of or under the bed sheet, clothing, or pillow, and the advantageous properties to modify the sound signals are selected and adjusted so as to still keep the produced rattling sound at reasonably low intensity to avoid disturbing the sleeping subject. The computer analysis software is monitoring at regular intervals the sound signals produced by the movements of the sleeping subject and classifies statistically the stages of the sleep into deep calm sleep, REM sleep, light sleep with arousals and awake state. The computer software utilizing e.g. filtering algorithms is adapted to reject noises or other acoustic interference with low frequency content connected to other phenomena than the movements of the sleeping subject. After the timer has indicated the beginning of the alarming time window, the computer software may have begun capturing and monitoring the sound signals continuously in real-time. After the analysis software, on the basis of the statistical analysis of the signals, has detected movements which are associated to light sleep with arousals or awake state (see the flow diagram of FIG. 4), the computer performs the wake-up procedure using e.g. the loudspeaker 22. If the software does not detect any signal epochs with probable awake state or light sleep with arousals during the awakening time window period, the alarming procedure is performed at the end time of the alarming window period, i.e. at the end of the awakening window. The user may preferably later utilize the display unit of his PDA to visually inspect the time and amplitude distribution of the movement signals detected during the night time.

The FIG. 3 visualizes a third advantageous embodiment of the present invention. In the FIG. 3 an electronic analysis and measuring device like a mobile cell phone 31 is supplied with a microphone 32, a loudspeaker 33, an alarming component with preferred vibration feature 34, and a display unit 35. The mobile cell phone may be e.g. a smart (intelligent) phone with one or more computer processors 36, a memory unit 37 and a timer unit 38. The computer analysis software 39 is stored in the processor to perform the processes described in the flow diagram of FIG. 4, for example. The user may be willing to follow up the sleep quality of another sleeping subject (like a baby or a child) and accordingly, he/she would like to receive an alarm indication if the sleeping subject is awake and not sleeping anymore. The mobile cell phone is located at near distance to the bed clothing of the sleeping subject e.g. under the pillow in a location that allows detecting the sound signals produced by the movements of the head and upper body of the sleeping subject against the pillow, for example. The computer analysis software 39 of the electronic device is activated by the user. The mobile cell phone 31 is sampling the sound signals associated to the movements of the sleeping subject at regular intervals. The software classifies the sound signal data statistically according to the flow diagram of FIG. 4, for example, to determine the probability that the sleeping subject is in calm peaceful deep sleep, in REM sleep or that the subject is moving during the awake state or during light sleep with arousals. The computer analysis software also advantageously stores the digital signal amplitude values in the memory unit 37 using the timer 38 at regular intervals. After detecting that with high probability the sleeping subject of the monitoring is in arousal or awakening phase and that the period of time of the awakening state is meaningful in duration, the alarming unit of the mobile cell phone may execute an alarm procedure by sending a message (such as a phone call, text message or other message) to an phone number pre-programmed to the phone. Alternatively, the cell phone may start monitoring the environment in a continuous manner for more precise analysis prior to triggering the alarm. On receipt of the alarm event the supervising party who is monitoring the well-being of the sleeping subject (e.g. the parents of the baby or the child) has indication to enter the room of the subject in order to investigate his state, and if the alarm procedure selected is a phone call, the supervising subject is capable of even listening to the sound signals transmitted by the phone (call) to detect if the baby or the child really is restless or whether he/she is falling asleep again without major interruptions.

The FIG. 4 includes a flow diagram of one possible embodiment of the method as carried out by the computer analysis software 9:

1. Execution of the computer analysis software is started and the user sets the awakening time period for the desired awakening moment incorporating both the earliest possible time of day to the alarm and the latest possible time of day (or awakening window length) to be awakened.
2. The timer is activated e.g. in the evening when the user goes to bed; the timer is used to monitor for the start of the awakening window.
2.1. During the sleep before the awakening time period (awakening time window), the timer may activate the analysis software to capture and analyse the sound signal at regular intervals using the microphone, wherein the amplitudes of the sound signals are preferably measured and the duration and amplitude data of the sound signals stored into the memory of the computer. The digital band-pass filtering may be used to reject the sound signals with low frequency contents and to eliminate sound transients as artefacts.
2.2 The statistical analysis of the signals is used to reject artefact signals by digital filtering, statistical parameters of the sound signals are calculated, e.g. the mean value or median filtering of the signals is applied, and the background noise level of the sound signals may be determined to detect the statistically typical sound signal levels and/or other parameters associated with sleeping and with movements.
2.3. The statistical analysis of the sound signals is used to determine the duration of the signals associated with movements of the sleeping subjects.
3. The start moment of the awakening time period (awakening window) is reached and another timer function may be activated.
3.1. Continuous sampling of the sound signals is preferably performed during the awakening time window.
3.2. The computer analysis software analyses the properties of detected sound signals to determine if the detected sound signal is above the statistically significant sound detection level which was present during the peaceful deep sleep prior to the awakening time window. In addition/alternatively other criteria may be applied.
3.3. The computer analysis software analyses the duration of the detected sound signals to determine if the duration of the detected sound signal is sufficient, according to criterion used, to indicate significant movements of the sleeping subject.
4.1. If the analysis software detects significant amount and duration of the movement signals, the alarm procedure of the electronic device is activated to wake up the sleeping subject.
4.2. If the function with a remote alarm message to the supervising person has been chosen, a message is sent to the pre-programmed phone number as a phone call or as a text message instead of an alarming procedure to wake up the sleeping subject.
5. If the analysis software does not detect any significant signals indicating movements due to arousals during the awakening time window, the sleeping subject is waked up at the end of the awakening time window using one or more alarming features of the electronic device.

The aforementioned examples represent only few advantageous embodiments of the method and the arrangement according to the present invention. The invention is not strictly limited to the aforementioned solutions as the related innovation may be adapted several ways still remaining within the scope of the appended claims.

The invention claimed is:

1. A method for detecting light sleep or arousal of a sleeping subject, comprising the steps of:
   operating an electronic device to perform the following sub-steps, said device being a portable electronic communication device or a portable data processing device,
   said device including
   i) a microphone to capture sound signals,
   ii) an alarm part to perform an awakening alarm function,
   iii) a power supply provided with sufficient capacity for operating said device over a predetermined operation time,
   iv) a memory, and
   v) a processor to operate the device,
   a) adaptively analysing the sound signals captured by the microphone both prior to a predetermined awakening-time window and during the awakening-time-window, wherein the analysis is executed more frequently during the awakening-time-window or a level of analysis changes for the awakening-time-window,
   the analyzing of the sound signals including an analysis of an amplitude of the sound signals, and at least one of the group consisting of spectral content of the sound signals, duration of the sound signals, and a distribution of the sound signals, and
   b) performing the awakening alarm function within the awakening-time-window when the analysis of the sound signals produced by movements of the subject during the awakening-time-window indicates ongoing light sleep or arousal from sleep, or that the end of the awakening-time-window is reached.

2. The method of claim 1, wherein, the electronic device and the microphone are surrounded by a predetermined material, the predetermined material selected for sound amplification and modifying properties of the sound signals, and
   comprising the further step of the predetermined material amplifying the sound signals produced by the movements of the sleeping subject and modifying the properties of the sound signals.

3. The method of claim 2, wherein,
said predetermined material is located i) surrounding the microphone, or ii) at a distance from the microphone,
the device is optimized to detect and recognize the sound signals produced by the said predetermined material located surrounding the microphone or at the distance from the microphone, and said sound signals are produced by the sleeping subject, and
said step of analyzing the sound signals produced by the sleeping subject, includes detecting and recognizing the sound signals produced by the said predetermined material located surrounding the microphone or at the distance from the microphone.

4. The method of claim 1, wherein,
the device further comprises a computer software pre-programmed into the memory of the device, the computer software to perform and complete said analysis step, and
the software has been loaded into the memory from an external source through the Internet.

5. The method of claim 1, wherein,
in the performing step, the wakening alarm function includes one of the group consisting of making a noise, making a sound, operating as buzzer, operating a light, and vibration of the device.

6. A portable electronic communication or data processing device for detecting light sleep or arousal, of a sleeping subject, comprising:
a microphone surrounded by a predetermined material for recording sound signals produced movements of the sleeping subject;
an alarm unit to perform an awakening alarm function; and
a power supply with sufficient capacity for performing predetermined operations over a predetermined operation time, a memory, and a processor to operate the device, wherein,
said device is configured to perform an adaptive analysis of the sound signals produced by the movements of the sleeping subject,
the microphone records the sound signals for the adaptive analysis both prior to a predetermined awakening-time window and during the awakening-time-window, wherein the analysis is executed more frequently during the awakening-time-window or a level of analysis changes for the awakening-time-window,
the analysis of the sound signals includes as analysis of an amplitude of the sound signals by the processor, and at least one of the group consisting of spectral content of the sound signals, duration of the sound signals, and a distribution of the sound signals, and
said device is configured to perform the awakening alarm function within the awakening-time-window when the analysis of the sound signals produced by movements of the subject during the awakening-time-window indicates ongoing light sleep or arousal from sleep, or that the end of the awakening-time-window is reached.

7. The device of claim 6, wherein,
the device includes a measuring apparatus and a predetermined material, the predetermined material being connected to the microphone located in a near distance to the measuring apparatus, and
said predetermined material is selected to amplify the sound signals produced by the movements of the sleeping subject and modify the properties of the sound signals.

8. The device of claim 6, wherein, the device is configured to wake up the sleeping subject being monitored with a feature of the device including one of the group consisting of sound, light, and vibration when the device detects one of the group consisting of the ongoing light sleep, the arousal from sleep, and reaching the end of the awakening-time-window.

9. The device of claim 6, wherein, the device is configured to operate the remote alarm of the device when the device detects one of the group consisting of arousal, awakening and wake state of the subject.

10. A method for detecting light sleep or arousal, comprising:
operating a portable electronic device to capture sound signals;
with the device, detecting the sound signals caused by movements of a sleeping subject both prior to a predetermined awakening-time window and during the awakening-time-window;
adaptively analysing the sound signals captured by the microphone both prior to the predetermined awakening-time window and during the awakening-time-window, wherein the analysis is executed more frequently during the awakening-time-window or a level of analysis changes for the awakening-time-window,
the analysing of the sound signals including an analysis of an amplitude of the sound signals, and one of the group consisting of spectral content of the sound signals, duration of the sound signals, and a distribution of the sound signals; and
performing the awakening alarm function within the awakening-time-window when the analysis of the sound signals produced by movements of the subject during the awakening-time-window indicates ongoing light sleep or arousal from sleep, or that the end of the awakening-time-window is reached,
wherein, a battery power supply of the device provides with sufficient capacity for operating i) the device over a predetermined operation time, ii) a memory with a pre-programmed software, and iii) a processor for said analyzing the amplitude, the spectral content, the duration, and the distribution of the detected sound signals.

11. The method of claim 1, wherein, the analysing step further includes, prior to entering the awakening-time window, determining background noise from the sound signals.

12. The method of claim 1, wherein, the analysing step further includes, prior to entering the awakening-time window, determining background noise from the sound signals utilizing median filtering.

13. The method of claim 1, wherein, the sound signals are captured and the analysis occurs at substantially regular intervals prior to the awakening-time-window and substantially continuously after entering the awakening-time-window.

14. The device of claim 6, wherein, the analysis of the sound signals further includes, prior to entering the awakening-time window, determining background noise from the sound signals.

15. The device of claim 6, wherein, the analysis of the sound sign further includes, prior to entering the awakening-time window, determining background noise from the sound signals utilizing median filtering.

16. The device of claim 6, wherein, the sound signals are captured and the analysis occurs at substantially regular intervals prior to the awakening-time-window and substantially continuously after entering the awakening-time-window.

17. The method of claim 10, wherein, the analysing step further includes, prior to entering the awakening-time window, determining background noise from the sound signals.

18. The method of claim 10, wherein, the analysing step further includes, prior to entering the awakening-time window, determining background noise from the sound signals utilizing median filtering.

19. The method of claim 10, wherein, the sound signals are captured and the analysis occurs at substantially regular intervals prior to the awakening-time-window and substantially continuously after entering the awakening-time-window.

20. The method of claim 1, wherein the method is executed by a mobile cell phone.

* * * * *

UNITED STATES PATENT AND TRADEMARK OFFICE
CERTIFICATE OF CORRECTION

PATENT NO. : 8,493,220 B2  Page 1 of 1
APPLICATION NO. : 12/527257
DATED : July 23, 2013
INVENTOR(S) : Virtanen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 890 days.

Signed and Sealed this
Eighth Day of September, 2015

Michelle K. Lee
*Director of the United States Patent and Trademark Office*